United States Patent
Chen et al.

(10) Patent No.: US 11,971,319 B2
(45) Date of Patent: Apr. 30, 2024

(54) SURFACE ELECTROMYOGRAPHY SIGNAL-TORQUE MATCHING METHOD BASED ON MULTI-SEGMENTATION PARALLEL CNN MODEL

(71) Applicants: QINGDAO TECHNOLOGICAL UNIVERSITY, Shandong (CN); XI'AN JIAOTONG UNIVERSITY, Xi'an (CN)

(72) Inventors: Cheng Jun Chen, Shandong (CN); Kai Huang, Shandong (CN); Dong Nian Li, Shandong (CN); Shuai Zheng, Shandong (CN); Jun Hong, Shandong (CN)

(73) Assignees: QINGDAO UNIVERSITY OF TECHNOLOGY, Shandong (CN); XI'AN JIAOTONG UNIVERSITY, Xi'an (CN)

(*) Notice: Subject to any disclaimer, the term of this patent is extended or adjusted under 35 U.S.C. 154(b) by 545 days.

(21) Appl. No.: 17/279,639

(22) PCT Filed: May 7, 2020

(86) PCT No.: PCT/CN2020/088876
§ 371 (c)(1),
(2) Date: Mar. 25, 2021

(87) PCT Pub. No.: WO2021/169036
PCT Pub. Date: Sep. 2, 2021

(65) Prior Publication Data
US 2022/0113206 A1    Apr. 14, 2022

(30) Foreign Application Priority Data
Feb. 25, 2020  (CN) .......................... 202010116661.6

(51) Int. Cl.
*G01L 3/02*    (2006.01)
*A61B 5/00*    (2006.01)
(Continued)

(52) U.S. Cl.
CPC ............... *G01L 5/24* (2013.01); *A61B 5/389* (2021.01); *A61B 5/6824* (2013.01);
(Continued)

(58) Field of Classification Search
CPC .......... G01L 5/24; A61B 5/389; A61B 5/6824
See application file for complete search history.

(56) References Cited

U.S. PATENT DOCUMENTS 7,062,979 B2 * 6/2006 Day ...................... B25B 23/147
                                                                73/862.22
11,331,045 B1 * 5/2022 Moschella ............. A61B 5/389
(Continued)

FOREIGN PATENT DOCUMENTS

| CN | 109816049 A | 5/2019 |
| CN | 110146213 A | 8/2019 |

(Continued)

OTHER PUBLICATIONS

International Search Report dated Dec. 1, 2020, issued in application No. PCT/CN2020/088876.

*Primary Examiner* — Lam S Nguyen
(74) *Attorney, Agent, or Firm* — McClure, Qualey & Rodack, LLP

(57) ABSTRACT

A surface electromyography signal-torque matching method based on multi-segmentation parallel CNN model (MSP-CNN model), step 1: collecting torque signals and surface electromyography (sEMG) signals when tightening a bolt; step 2: dividing a range of a transducer by at least two granularities, generating a plurality of torque sub-ranges corresponding to the at least two granularities and labeling
(Continued)

the plurality of torque sub-ranges with torque labels; step 3: generating sEMG graphs of the sEMG signals in each time window; step 4: determining the torque labels of each time window under each of the at least two granularities according to the torque sub-ranges that average values of torques fall in; step 5: establishing a sample set; step 6: building a MSP-CNN model, and training parallel independent CNN models with sample datasets; and step 7: inputting the sEMG signals of the operator during assembly into trained MSP-CNN model and identifying assembly torques.

10 Claims, 2 Drawing Sheets

(51) Int. Cl.
*A61B 5/389* (2021.01)
*G01L 5/24* (2006.01)
*G06T 11/20* (2006.01)

(52) U.S. Cl.
CPC .......... *A61B 5/6831* (2013.01); *A61B 5/7264* (2013.01); *G06T 11/206* (2013.01)

(56) References Cited

U.S. PATENT DOCUMENTS

| 2011/0164657 A1* | 7/2011 | Coffland | G01S 5/0205 |
| | | | 375/E1.001 |
| 2014/0182393 A1 | 7/2014 | Heinkel et al. | |
| 2020/0273177 A1 | 8/2020 | Chen et al. | |

FOREIGN PATENT DOCUMENTS

| CN | 110210366 A | 9/2019 |
| CN | 110672312 A | 1/2020 |
| JP | 4049989 B2 * | 2/2008 |

* cited by examiner

SURFACE ELECTROMYOGRAPHY SIGNAL-TORQUE MATCHING METHOD BASED ON MULTI-SEGMENTATION PARALLEL CNN MODEL

TECHNICAL FIELD

The present invention relates to a surface electromyography signal-torque matching method based on multi-segmentation parallel CNN (Convolutional Neural Networks) model, and belongs to product assembly monitoring and intelligent manufacturing field.

BACKGROUND TECHNOLOGY

Exerting accurate tightening torque is one of important measures to enhance bolt connection property and improve product assembly quality. Currently, due to limitation from assembly space and efficiency, wrenches with no torque measuring function are still a widely used assembly tool. Therefore, real-time torque monitoring of wrenches remains an urgent problem to be solved. At present, common assembly torque monitoring tools are torque measuring wrenches, preset fixed torque wrenches, and torque stress testers etc. By using a torque measuring wrenches it is possible to observe torque during bolt assembly on a real-time basis. However, it is necessary for the operators to know torque standards for bolts of different sizes, and during tightening process, over-tightening or slip of bolt threads is liable to happen; with a preset fixed torque wrench, it is not possible to monitor torque in real time, however, by setting a torque value for bolt tightening, firmness of connection between parts can be promised, and over-tightening or slip of bolt threads can be avoided; and by deploying a bolt torque stress tester, it is possible to monitor in real time loosening conditions of high strength bolts during use, however, this method is only applicable for monitoring after product assembly, with a belated monitoring result, and hypersonic elements and piezoelectric elements in the bolt torque stress tester are subject to influences from using environment.

Surface electromyography (sEMG) signals are one dimensional temporal signals reflecting neuromuscular system activities, which reflect directly characteristics of human motions, and are widely used in medicine, rehabilitation medicine and human-computer interaction fields. With sEMG signals, it is possible to estimate human muscular forces that cannot be calculated precisely, and sEMG signals can be applied in action recognition and muscular force prediction. Therefore, the present invention proposed to use sEMG signals to monitor tightening torques during product assembly.

SUMMARY OF THE INVENTION

To address the abovementioned problems, the present invention provides a surface electromyography signal-torque matching method based on multi-segmentation parallel CNN (Convolutional Neural Networks) model and by acquiring surface electromyography signals and inputting into the multi-segmentation parallel CNN model, torque values can be known and used in monitoring tightening torque in real time and accurately.

Technical solutions of the present invention are as following: A surface electromyography signal-torque matching method based on multi-segmentation parallel CNN model, comprising following steps: step 1: collecting and saving torque signals and electromyography signals of an operator when tightening a bolt on a test bench; step 2: dividing a range of a tightening torque transducer on the test bench according to at least two granularities, a plurality of torque sub-ranges corresponding to each of the at least two granularities are generated and labeling each of the torque sub-ranges with a torque label; step 3: generating sEMG graphs of the sEMG signals with every t seconds a time window; step 4: calculating average values of all the torque signals in each time window, determining the torque labels of each time window under each of the at least two granularities according to the torque sub-ranges that the average values of torques fall in; step 5: establishing a sample set, which comprises sample datasets of the at least two granularities, a sample dataset of each of the at least two granularities comprises a plurality of sEMG graphs with torque labels, granularities corresponding to the torque labels are the same as granularities corresponding to the sample datasets and the time windows corresponding to the torque labels are the same as the time windows corresponding to the sEMG graphs; step 6: building a multi-segmentation parallel CNN model, which contains at least two parallel independent CNN models, with a classification granularity of sEMG signals in each of the at least two parallel independent CNN models different, and sample datasets with the same granularity will be used to train corresponding independent CNN models; and step 7: inputting sEMG signals of the operator during assembly into the trained multi-segmentation parallel CNN model and identifying assembly torques.

Preferably, in the step 1, N channels are deployed to acquire the sEMG signals simultaneously; in the step 3, preprocessing acquired sEMG signals in each of the N channels, and normalizing all the sEMG signals in each of the N channels; drawing sEMG graphs corresponding to all the time windows, with each of the sEMG graphs containing normalized sEMG signals of all the channels in one of the time windows.

Preferably, normalize the sEMG signals by applying a formula (1)

$$A'_i = \frac{A_i - A_{min}}{A_{max} - A_{min}},$$

map the sEMG signals to a range of [0, 1]; wherein, $A_{max}$ stands for a maximum value of the sEMG signals in all the N channels; $A_{min}$ stands for a minimum value of the sEMG signals in all the N channels; $A_i$ is the i-th sEMG value, and $A'_i$ is a max-min normalized value of the i-th sEMG signal.

Preferably, the step 4 is: standardizing the torque signals and getting an average value; standardization of the torque signals is done as per a following equation and get $T'_i$, wherein $l_i$ is a length of an i-type wrench, $l_{max}$ is a length of a longest wrench, $T_i$ is a torque value measured of the i-type wrench, and $T'_i$ is a standardized torque value of the i-type wrench;

The standardization equation is $$T'_i = l_{max} T_i / l_i.$$

Preferably, the step 6 is: inputting surface electromyography graphs with torque labels into each of the independent CNN models, with granularities of the torque labels consistent with granularities of the models, outputting the torque labels, and fusing the output torque labels from each of the independent CNN models as estimated torque values of the MSP-CNN model.

Preferably, said fusion is done by: taking medians of the torque sub-ranges corresponding to torque labels with a highest probability outputted from the CNN models of each of the granularities, and calculating average values of all the medians as estimated torque value of the MSP-CNN model.

Preferably, preprocessing of acquired sEMG signals of all the channels comprising following steps: passing the acquired sEMG signals through a 50 Hz low-pass notch filter and a 30 Hz zero-phase-shift high-pass filter, inverting negative values of the sEMG signals, and passing through a 5 Hz zero-phase-shift high-pass filter for filtering to stimulate low-pass filtering characteristics of muscles; wherein, the 50 Hz low-pass notch filter is used to eliminate interference from local frequencies to the sEMG signals and the 30 Hz zero-phase-shift high-pass filter is used to clear motion artifacts of the received sEMG signals.

Preferably, after standardizing the torque signals, preprocess in a following manner and calculating the average values, the preprocessing is done by: applying the 50 Hz low-pass notch filter to the torque signals to eliminate impacts of the local frequencies on signal acquisition and subsequently, applying the 30 Hz zero-phase-shift high-pass filter to the processed torque signals for filtering and removing motion artifacts.

Preferably, in the step 1, a wearable device is worn on the operator to acquire the sEMG signals.

Preferably, the wearable device is an MYO armband.

The present invention has following beneficial effects:

1) By the surface electromyography signal-torque matching method based on multi-segmentation parallel CNN model according to the present invention, a multi-segmentation parallel CNN model is used to extract torque values during tightening a bolt from sEMG signals of the operator, and realize real-time monitoring of tightening torques during product assembly.
2) With the surface electromyography signal-torque matching method based on multi-segmentation parallel CNN model according to the present invention, sEMG signals can be collected by merely including a wearable device on the operator and it is convenient to monitor tightening torques.
3) By the surface electromyography signal-torque matching method based on multi-segmentation parallel CNN model according to the present invention, output results from a plurality of CNN models with different granularities are fused together to get a finer torque classification and improve accuracy of torque prediction. The multi-segmentation parallel CNN model can improve accuracy of torque prediction when ensuring all the CNN models are converging rapidly.

EMBODIMENTS

Hereinafter a detailed description will be given to the present invention by way of the accompanying drawings and embodiments.

Figure 1:
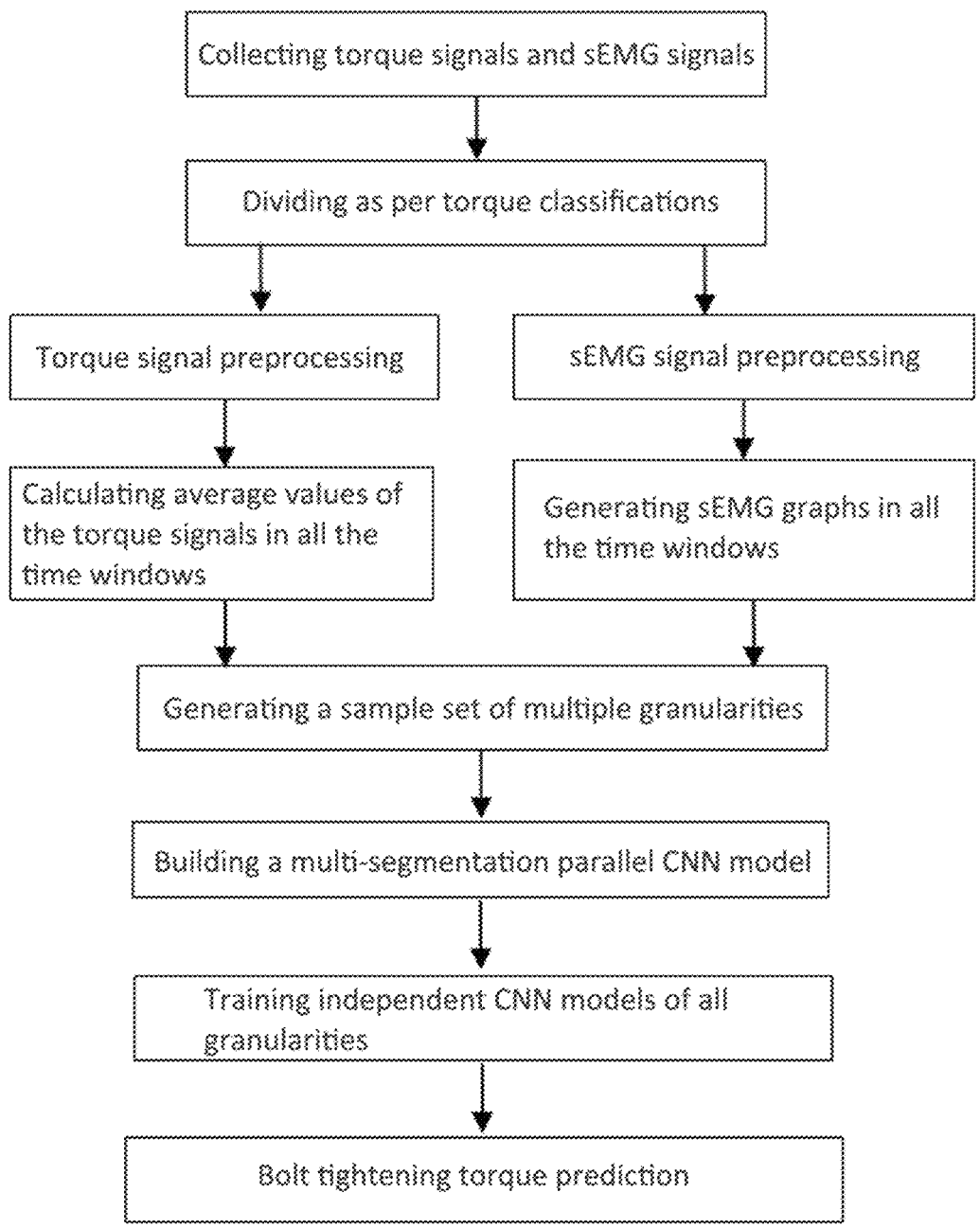
FIG. 1 is a flowchart diagram showing a surface electromyography signal-torque matching method based on multi-segmentation parallel CNN model according to the present invention.
Figure 2:
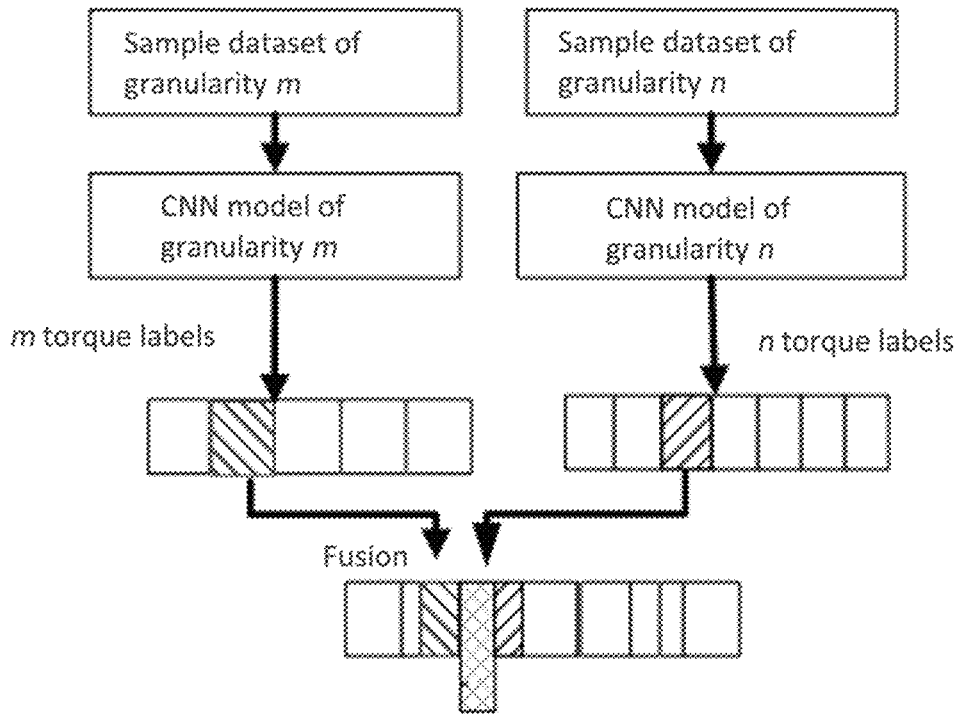
FIG. 2 is a flowchart diagram showing a sample training process according to the present invention.

As is shown in FIG. 1 and FIG. 2, a surface electromyography signal-torque matching method based on multi-segmentation parallel CNN (Convolutional Neural Networks) model, comprising following steps:

Step 1: collecting and saving torque signals and sEMG signals when an operator is tightening a bolt on a test bench, and sEMG signal acquisition can be done by a wearable device, such as an MYO armband supporting Bluetooth communication, so it is not necessary to add a transducer on the wrench or the assembly bench, which involves strong human computer interaction and is of good utilization value.

Figure 3:
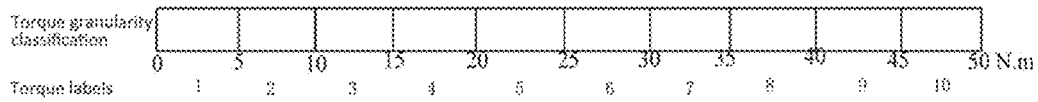
FIG. 3 is a diagram showing granularity classification of a range in the present invention.

Step 2: dividing a range of a transducer for measuring the torque signals of tightening force on the test bench to at least two granularities, and hereinafter implementation of the present embodiment will be elaborated by dividing the range into a granularity of m and a granularity of n. When the transducer range is divided as per a granularity classification, a plurality of torque sub-ranges corresponding to the granularity are generated, and add a torque label to each of the plurality of torque sub-ranges; as shown in FIG. 3, take a transducer with a range of 0~50N·m for example, divide torque values in the torque range evenly into ten torque sub-ranges, that is, conducting a ten-granularity equalization, into respectively [0, 5), [5, 10), [10, 15), [15, 20), [20, 25), [25, 30), [30, 35), [35, 40), [40, 45), and [45, 50), with a unit of N·m, and give a torque label to each of the torque sub-ranges, such as in the figures, the torque label of [0, 5) is 1, the torque label of [5, 10) is 2 etc. And as per the foregoing method, the torque range can be divided equally by a granularity of 5, 10, and 20 etc.

Step 3: setting every t seconds a time window and generating sEMG graphs of the sEMG signals corresponding to the time window, generally, t is no more than 0.5 second; taking as an example of collecting eight-channel sEMG signals with a following implementation process:

Preprocessing: (1) applying a 50 Hz low-pass notch filter to process the eight-channel sEMG signals, to eliminate interference from local frequencies to the sEMG signals; (2) applying a 30 Hz zero-phase-shift high-pass filter to the sEMG signals after processing in (1) to clear motion artifacts; (3) inverting negative values of the signals; and (4) applying a 5 Hz zero-phase-shift low-pass filter for filtering to stimulate low-pass filter characteristics of muscles.

Normalization: applying an equation (1)

$$A'_i = \frac{A_i - A_{min}}{A_{max} - A_{min}}$$

to give a max-min normalization treatment to the sEMG signals, and projecting the sEMG signals on a range of [0, 1] to convert the sEMG signals to scalar data and eliminate effects of vectors. Among that, $A_{max}$ stands for a maximum value of the sEMG signals in all the N channels; $A_{min}$ stands for a minimum value of the sEMG signals in all the N channels; $A_i$ is the i-th sEMG value, and $A'_i$ is a max-min normalized value of the i-th sEMG signal.

Drawing sEMG graphs: drawing respectively sEMG graphs corresponding to the time windows, with each of the sEMG graphs containing normalized sEMG signals of all the channels in each of the time windows. Specifically, taking for example a sampling frequency f of 200 Hz, and 0.5 second a time window: starting from the same time, eight-channel sEMG signals of every 0.5 s are drawn into an sEMG graph, that is, in every time window, there are f*t normalized sEMG signals of all eight channels and in the present example, f*t=100, therefore, dimension of each of the sEMG graphs is (100, 8), and 8 represents the eight channels of the sEMG signals.

Step 4: calculating average values of all the torque values of the torque signals in each of the time windows, and determining the torque labels of the time windows by the torque sub-ranges that the average values of the torque values fall in, specifically comprising:

Standardization of the torque signals: standardizing the torque signals according to a formula to get $T'_i$, wherein $l_i$ is a length of an i-type wrench, $l_{max}$ is a length of a longest wrench, $T_i$ is a torque value measured of an i-type wrench, and $T'_i$ is a standardized torque value of the i-type wrench;

And the formula is:

$$T'_i = l_{max} T_i / l_i.$$

Torque signal preprocessing: applying a 50 Hz low-pass notch filter to the standardized torque signals to eliminate impacts on the signal acquisition resulted from local frequencies and employing a 30 Hz zero-phase-shift high-pass filter to filter and erase motion artifacts.

Determining torque labels of the sEMG graphs: calculating average values of the torque signals according to length of signals in the sEMG graphs (length of the time windows), calculating an average value for torque signals in every t seconds as the average value of the torque signals in the present time window, which can ensure the average values of the torque signals correspond to the sEMG graphs in a time sequence. Checking in different granularity classifications the torque sub-ranges that the average values of the torque signals fall in, determining the torque labels, and generating corresponding torque labels for each of the time windows in different granularity classifications; for example, when granularity classification is m, an average value of the torque signals falls in a torque sub-range of (10~15), corresponding to a torque label of A, and when granularity classification is n, the average value of the torque signals falls in a torque sub-range of (10~20) and corresponds to a torque label of a. Therefore, torque labels of each of the sEMG graphs vary when the granularity classification is different.

Step 5: establishing a sample set, which comprising sample dataset of at least two granularities, the sample dataset for each of the at least two granularities comprises a plurality of sEMG graphs with torque labels, the granularities corresponding to the torque labels are the same as the granularities corresponding to the sample dataset, and the time windows corresponding to the torque labels are the same as the time windows corresponding to the sEMG graphs; for example, in a dataset with a granularity of m, each of the sEMG graphs is tagged a torque label of granularity m, and in a dataset with a granularity of n, each of the sEMG graphs is tagged a torque label of granularity n.

As is shown in FIG. 2, step 6: building a multi-segmentation parallel CNN model, which comprises at least two independent parallel CNN models, granularity classifications of the sEMG signals in each of the at least two independent parallel CNN models are different and using sample datasets of the same granularity to train corresponding independent CNN models. Specifically, inputting sEMG graphs with torque labels into each of the at least two independent parallel CNN models with the granularities corresponding to the torque labels consistent with classification granularities of the models, classifying the sEMG signals by CNN network, and outputting the torque labels. Fusing the output torque labels from each of the at least two independent parallel CNN models as predicted torque values of the multi-segmentation parallel CNN model. Fusing the output results from the plurality of CNN models with different granularities to get a torque classification with finer granularity and improve accuracy of torque prediction.

Said fusing can be done in a following manner: taking medians of the torque sub-ranges corresponding to the torque labels output from each of the at least two independent parallel CNN model with the greatest probability, and calculating an average value of all the medians as a predicted torque value of the multi-segmentation parallel CNN model. For example, when the medians of the torque sub-ranges corresponding to the torque labels outputted by an independent CNN model with a granularity of m and another independent CNN model with a granularity of n is $T_m$ and $T_n$, take $(T_m+T_n)/2$ as a torque value predicted by the multi-segmentation parallel CNN model, and a grid square portion in the FIG. 2 represents output torque labels after fusion.

Step 7: inputting sEMG signals of the operator during actual assembly process into the trained multi-segmentation parallel CNN model and identifying the assembly torque.

It shall be supplemented that, the following CNN model architect can be used in the present invention.

Figure 4:
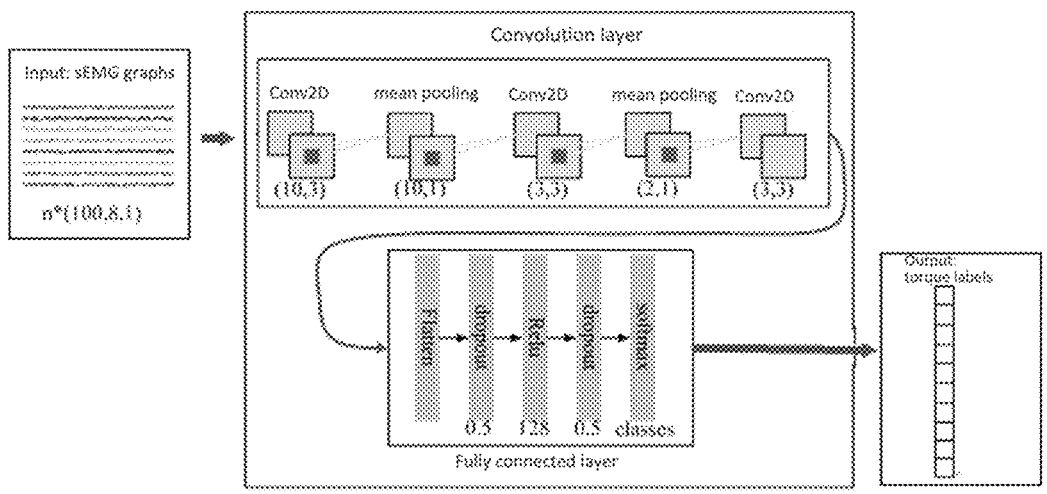
FIG. 4 is a diagram showing CNN models according to the present invention.

As is shown in FIG. 4, an inputting layer: the inputting layer comprising preprocessed sEMG graphs, with a dimension of (100, 8, 1) and n stands for n sEMG graphs.

Convolution layer: the convolution layer comprising three convolutional computations and two pooling computations. A purpose of convolutional computation is to extract features of the sEMG graphs, add bias to it, and activate with an activation function. The number of filters in the first convolutional computation is 32, size of the convolutional kernel is (10, 3), step size of the convolutional computation is (1, 1) and an activation function used is ReLU; the number of filters for the second convolutional computation is 64, size of the convolutional kernel is (3, 3), step size of the convolutional computation is (1, 1) and the activation function is ReLU; the number of filters for the third convolutional computation is (1, 1), size of the convolutional kernel is (3, 3), step size of the convolutional computation is (1, 1), the activation function uses ReLU, and the filling layer uses VALID. The pooling computation, also called down-sampling computation, aims to reduce parameters while preserving main features, reduce a phenomenon of overfitting, and improve generalization ability of the model. Based on performance comparison, average pooling is adopted in the present invention; pooling size of the first pooling computation is (10, 1); pooling size for the second pooling computation is (2, 1).

Fully connected layer: the fully connected layer includes flatten computations, two dropout computations and fully connected neural network computations. Flatten computation is a kind of dimension reducing and expansion computation and a purpose of flattening computation is to reduce 2D data after Conv2D computation into 1D data without affecting size of batch processing. Dropout calculation is to solve a phenomenon of easy overfitting caused by few training samples and many model parameters. The fully connected neural network classifies and calculates 1D data according to preset labels, where the number of the filters is 128, and the activation function is ReLU.

Softmax layer: the softmax layer is used as an output layer to output the torque classification results and map the output results to (0, 1), representing a probability value of the torque classification results.

To summarize, the surface electromyography signal-torque matching method based on multi-segmentation parallel CNN model according to the present invention makes use of the multi-segmentation parallel CNN model, extracts torque values of bolt tightening from sEMG signals of the operator and realizes real-time monitoring of the tightening torques during product assembly. It is convenient to monitor in real-time the tightening torque as the sEMG signals can be collected by only wearing a wearable device on the operator. In the meantime, the present invention fuses output results from a plurality of CNN models with different granularities to get a torque classification with a finer granularity and improve accuracy of torque prediction. The multi-segmentation parallel CNN model can improve accuracy of torque prediction of the entire model when promising all the CNN models are converging quickly.

The foregoing are only some embodiments of the present invention without limiting protection scope of the present invention thereto, and all equivalent structures or flow process alterations made based on specification and drawings of the present invention or use directly or indirectly in other relevant technical fields are covered in the protection scope of the present invention.

We claim:

1. A surface electromyography signal-torque matching method based on multi-segmentation parallel CNN model, comprising following steps:
   (Step 1): collecting and saving torque signals and surface electromyography (sEMG) signals of an operator when tightening a bolt on a test bench;
   (Step 2): dividing a range of a tightening torque transducer on the test bench according to at least two granularities, generating a plurality of torque sub-ranges corresponding to each of the at least two granularities and labeling each of the plurality of torque sub-ranges with a torque label;
   (Step 3): generating sEMG graphs of the sEMG signals with every t seconds a time window;
   (Step 4): calculating average values of all the torque signals in each time window, determining the torque label of each time window under each of the at least two granularities according to the torque sub-ranges that the average values of torques fall in;
   (Step 5): establishing a sample set comprising sample datasets of at least two granularities, each of the sample datasets of each of the at least two granularities comprises a plurality of sEMG graphs with torque labels;
   (Step 6): building a multi-segmentation parallel CNN model, containing at least two parallel independent CNN models, with classification granularities of the sEMG signals in each of the at least two parallel independent CNN models different, and training the at least two parallel independent CNN models with sample datasets with the same granularity; and
   (Step 7): inputting the sEMG signals of the operator during assembly into the trained multi-segmentation parallel CNN model and identifying assembly torques.

2. The surface electromyography signal-torque matching method based on multi-segmentation parallel CNN model according to claim 1, wherein: in the (step 1), N channels are used to collect the sEMG signals simultaneously, N is a natural number; and in the (step 3), preprocessing the sEMG signals collected through the channels, and normalizing the sEMG signals from all the channels; drawing the sEMG graphs corresponding to each time window, and in each of the sEMG graphs are normalized sEMG signals of all the channels in each time window.

3. The surface electromyography signal-torque matching method based on multi-segmentation parallel CNN model according to claim 2, wherein normalization of the sEMG signals is done by applying an equation (1), and mapping the sEMG signals to a range of [0, 1]; wherein, Amax is a maximum value of the sEMG signals in N channels; Amin is a minimum value of the sEMG signals in N channels; Ai is a value of the i-th sEMG signal and A'I is a value after normalization of the i-th sEMG signal.

4. The surface electromyography signal-torque matching method based on multi-segmentation parallel CNN model according to claim 1, characterized in that, the step 4 is: standardizing the torque signals and calculating the average values thereof; standardization of the torque signals is done as per a following formula to get Ti', wherein, li is length of an i-type wrench, lmax is length of a longest wrench, Ti is a torque value measured under the i-type wrench and Ti' is a standardized torque value measured under the i-type wrench;

The standardizing formula is: $Ti'=l\max Ti/li$.

5. The surface electromyography signal-torque matching method based on multi-segmentation parallel CNN model according to claim 1, characterized in that, the step 6 is: inputting the sEMG graphs with the torque labels into the at least two parallel independent CNN models with the granularities corresponding to the torque labels consistent with the granularities of the at least two parallel independent CNN model; outputting as the torque labels, and fusing output torque labels from each of the at least two parallel independent CNN models together as predicted torque values of the multi-segmentation parallel CNN model.

6. The surface electromyography signal-torque matching method based on multi-segmentation parallel CNN model according to claim 5, characterized in that, said fusing is done by: taking a median of the torque sub-range corresponding to the torque label with a highest probability from each of the at least two parallel independent CNN models of different granularities, and calculating average values of all the medians as the predicted torque values of the multi-segmentation parallel CNN model.

7. The surface electromyography signal-torque matching method based on multi-segmentation parallel CNN model according to claim 5, characterized in that, preprocessing the sEMG signals from all the channels comprising following steps: passing the sEMG signals sequentially through a 50 Hz low-pass notch filter and a 30 Hz zero-phase-shift high-pass filter, inverting negative values in the sEMG signals and passing through a 5 Hz zero-phase-shift low-pass filter for filtering to stimulate low-pass filter characteristics of muscles; wherein, the 50 Hz low-pass notch filter is to eliminate interference from local frequencies to the sEMG signals and the 30 Hz zero-phase-shift high-pass filter is to clear motion artifacts in collected sEMG signals.

8. The surface electromyography signal-torque matching method based on multi-segmentation parallel CNN model according to claim 4, characterized in that, after standardizing the torque signals, preprocessing in a following manner and thereafter calculating the average values: applying a 50 Hz low-pass notch filter to the torque signals to eliminate impacts from local frequencies to signal collection and applying a 30 Hz zero-phase-shift high-pass filter to the processed torque signals to clear motion traces.

9. The surface electromyography signal-torque matching method based on multi-segmentation parallel CNN model according to claim 1, characterized in that, in the step 1, sEMG signals collection is done by wearing a wearable device on the operator.

10. The surface electromyography signal-torque matching method based on multi-segmentation parallel CNN model according to claim 9, characterized in that, the wearable device is a MYO armband.

\* \* \* \* \*